(12) United States Patent
Jorgensen et al.

(10) Patent No.: US 6,439,577 B2
(45) Date of Patent: Aug. 27, 2002

(54) ROTATING SEALS FOR CELL PROCESSING SYSTEMS

(75) Inventors: Glen Jorgensen, Marlboro; Donald Barry, Norwood; Mark Susser, Weston, all of MA (US)

(73) Assignee: Zymequest, Inc., Beverly, MA (US)

(*) Notice: Subject to any disclaimer, the term of this patent is extended or adjusted under 35 U.S.C. 154(b) by 0 days.

(21) Appl. No.: 09/760,684

(22) Filed: Jan. 16, 2001

Related U.S. Application Data

(63) Continuation of application No. 09/081,733, filed on May 20, 1998, now abandoned.
(60) Provisional application No. 60/047,213, filed on May 20, 1997.

(51) Int. Cl.[7] .............................. F16J 15/34; F16L 27/00
(52) U.S. Cl. ........................ 277/374; 277/375; 277/401; 277/405; 277/907; 285/121.6
(58) Field of Search .................................. 277/370, 374, 277/375, 380, 401, 405, 907, 364, 371; 285/121.6, 124.1, 124.3

(56) References Cited

U.S. PATENT DOCUMENTS

| | | | |
|---|---|---|---|
| 1,618,655 A | * | 2/1927 | Halvorsen |
| 2,148,093 A | * | 2/1939 | Wheeler |
| 2,586,739 A | * | 2/1952 | Summers |
| 2,902,301 A | * | 9/1959 | Daeschner |
| 3,015,506 A | * | 1/1962 | Tracy |
| 3,489,145 A | * | 1/1970 | Judson et al. |
| 3,565,330 A | * | 2/1971 | Latham et al. |
| 4,300,717 A | * | 11/1981 | Latham et al. |
| 4,387,848 A | | 6/1983 | Kellogg et al. ............... 494/81 |
| 4,767,396 A | * | 8/1988 | Powers |
| 5,045,048 A | | 9/1991 | Kaleskas et al. .............. 494/41 |
| 5,386,734 A | | 2/1995 | Pusinelli .................... 73/863.2 |
| 5,676,644 A | | 10/1997 | Toavs et al. .................... 604/4 |

FOREIGN PATENT DOCUMENTS

| | | | |
|---|---|---|---|
| EP | 0 682 953 A1 | 11/1995 | ........... A61M/1/36 |
| WO | PCTWO96/28199 | 9/1996 | ........... A61M/1/36 |

OTHER PUBLICATIONS

Communication from the International Searching Authority dated Jul. 9, 1998 (6 pages)

* cited by examiner

Primary Examiner—Anthony Knight
Assistant Examiner—Vishal Patel
(74) Attorney, Agent, or Firm—Ivor R. Elrifi; Brian P. Hopkins, Esq.; Mintz, Levin, Cohn, Ferris, Glovsky and Popeo, P.C.

(57) ABSTRACT

The invention provides an improved rotating seal apparatus including a plurality of concentrically spaced annular rotating seals. The invention also provides a rotating seal apparatus including a pressurized annular chamber surrounding an annular rotating seal.

12 Claims, 9 Drawing Sheets

ROTATING SEALS FOR CELL PROCESSING SYSTEMS

RELATED APPLICATION

This application is a continuation of Ser. No. 09/081,733 filed May 20, 1998, now abandoned, and claims the benefit under Title 35. U.S.C. §119(e) of pending U.S. Provisional Application Serial No. 60/047,213, filed May 20, 1997 entitled "Cell Processing System", incorporated herein by reference. This application is also related to co-pending U.S. Patent Applications entitled: "Apparatus and Method for Expressing Fluid Materials"; (Ser. No. 09/082,200); "Fluid Management Systems"(Ser. No. 09/082,201); "Optical Sensors for Cell Processing Systems"(Ser. No. 09/082,086); and "Cell Processing Systems"(Ser. No. 09/082,341), all of which are incorporated by reference.

FIELD OF THE INVENTION

The invention relates to rotating seals for centrifugal devices useful, inter alia, in cell processing or cell washing applications.

BACKGROUND OF THE INVENTION

Generally, cell processing requires steps in which cells or cell elements are separated from a liquid phase. This separation is typically accomplished by centrifugation. The sterility of the cells being processed is protected by the incorporation of a dynamic seal between rotatable and stationary centrifuge elements, referred to as a "rotating seal". In addition to deterring the entrance of microbes into the sterile environment of the processing apparatus and the biological materials contained therein, a rotating seal ideally minimizes the leakage of air and frictional heating and is capable of tolerating mild to moderate misalignment and vibration.

A number of designs for rotating seals have been developed. For example, U.S. Pat. No. 3,489,145 by Judson et al. discloses a lower rotating element that forms a seal with an upper stationary element, and that has a central bore extending throughout. U.S. Pat. Nos. 3,409,203 and 3,565,330 by Latham disclose rotating seals formed from a stationary rigid low-friction element in contact with a moving rigid element and an elastomeric element which provides a resilient static seal as well as a modest closing force between the seal surfaces. U.S. Pat. No. 3,801,142 by Jones et al. relates to a pair of elements having confronting annular fluid-tight sealing surfaces maintained in a rotatable but fluid-tight relationship by axial compression of a length of elastic tubing. In the "B. T. Bowl" marketed by Bellco (Mirandola, Italy), a rotating seal is formed between a ceramic ring element attached to rotatable elements of a centrifuge and a fixed graphite ring attached to stationary centrifuge elements; an elastomeric diaphragm is attached at one end to an adapter ring for the graphite ring and at the other end to a stationary part of the centrifuge. U.S. Pat. Nos. 4,300,717 and 5,045,048 by Latham, Jr. relate to a rotating seal which has been modified by the incorporation of recessed areas contiguous with "sealed" regions; the recessed areas are in communication with the external environment and are used to entrap and expel extraneous particles which may form during centrifugation.

In the field of centrifugal cell washing, two technologies currently dominate the state of the art, as exemplified by the Cobe 2991 and the Haemonetics Model 115 cell washers. Both systems employ a set of rotating seals to contain the fluids in the disposable rotating containers. These seals have been classified by the FDA as "open" devices for the purpose of washing red blood cells, in that the seals have not yet been validated as having the ability to satisfactorily prevent biological contamination of the sterile interior under all running and handling conditions. According to the American Association of Blood Banks ("AABB") standards, "when glycerolizing or deglycerolizing involves entering the container, the system is considered 'open' and the resulting suspension of deglycerolized cells can be stored for only 24 hours at 1–6 degrees Centigrade." This 24-hour storage shelf life after deglycerolization, and other factors (including cost), make the foregoing systems less useful for routine inventory management and relegate them primarily to specialty uses such as storing rare blood types, autologous donations, or battlefield applications for the Navy.

None of the foregoing rotating seals provides a seal which permits the storage of processed biological materials such as red blood cells for extended period of time. The foregoing seals do not provide adequate protection from the contamination of processed biological materials by microbial contaminants.

SUMMARY OF THE INVENTION

The invention provides an improved rotating seal which provides enhanced anticontamination properties for use in particular in centrifugal devices for processing biological materials. The seal of the invention comprises at least two concentrically spaced rotating seals, wherein the annular space between the seals forms at least one sterile chamber. In the event of a leak in one of the concentrically spaced rotating seals, the additional seal or seals act to maintain the sterile environment of the cell processing system by reducing or preventing microbial contamination. In addition, the sterile annular chamber can be pressurized with a sterile supply of gas as a second means of reducing or preventing microbial contamination. The pressurized chamber acts as a barrier to prevent microbes from migrating into the interior of the cell processing system across a leaky seal. The pressurized chamber also acts as a barrier to reduce or prevent the migration of fluids or particulate matter from the interior of the cell processing system across the a leaky seal.

According to one aspect of the invention, an improved cell processing system is provided, the improvement comprising a plurality of annular rotating seals between rotating and non-rotating portions of the cell processing system. The plurality of annular rotating seals define at least one annular space between the annular rotating seals. The at least one annular space is constructed and arranged for receiving pressurized gas. In some embodiments, the plurality of annular rotating seals includes a plurality of sealing members defining annular sealing surfaces which form a plurality of concentrically spaced annular rotating seals, the annular rotating seals defining at least one annular space. At least one of the sealing members defines a channel in a non-sealing surface, which channel is in gaseous communication with the at least one annular space. Preferably the at least one annular space is pressurized with gas. In certain preferred embodiments, the annular sealing surfaces are substantially planar. In other embodiments, the apparatus also includes a body defining a gas port, wherein the gas port is in gaseous communication with the channel. The apparatus also can include a pressure sensor in communication with the gas port for monitoring the gas pressure in the annular space.

According to another aspect of the invention, a seal apparatus is provided. The seal includes plurality of annular seal members. A first annular rotating seal member includes a sealing face which defines a plurality of concentrically spaced annular sealing surfaces, and an axial opening. A second annular rotating seal member has a sealing face which defines at least one annular sealing surface, and an axial opening. The first annular rotating seal member and the second annular rotating seal member are axially aligned and the annular sealing surfaces are placed in contact to form a plurality of spaced apart seals. Preferably the annular sealing surfaces are substantially planar. In certain embodiments, the sealing face of the first sealing element further defines an annular space between the annular sealing faces. The annular sealing surfaces can be biased together by a bias element, which preferably is an elastomeric spring element. The annular sealing surfaces are preferably formed of a material selected from the group consisting of ceramics, carbon phenolic and equivalent carbon composite materials; more preferably, all annular sealing surfaces are formed of ceramic materials. In other embodiments, at least one of the non-sealing faces of the first annular rotating seal member and the second annular rotating seal member define a channel in gaseous communication with the annular space.

The seal apparatus also can include a body which includes a first port disposed in the axial openings of the first and second annular rotating seal members. Preferably at least one of the no[008e] sealing faces of the first annular rotating seal member and the second annular rotating seal member define a channel in gaseous communication with the annular space, wherein the body includes a gas port in communication with the channel. The seal apparatus also includes in some embodiments a base having an axial opening and a processing container having a top defining an axial opening. The base is mounted in axial alignment on the top of the processing container, and the second annular rotating seal member mounted in axial alignment on the top surface of the base. Thus assembled, the first port of the seal apparatus is in fluid communication with the interior of the processing container. Preferably the first port extends through the axial openings of the first and second annular rotating seal members and the base. The body also can include a fluid port in fluid communication with the space defined by the first port, the first and second annular rotating seal members and the axial opening of the base. In additional embodiment, the seal apparatus includes an outer shield defining a space between the outer shield and the body, the base and the first and second annular rotating seal members. Preferably the outer shield comprises a shield top, a shield bottom and a shield clamp, wherein the shield top is releasably mounted on the shield bottom, and wherein shield bottom and shield clamp have overlapping flanges which form a serpentine seal. In certain embodiments, the diameter of the shield bottom is smaller than the diameter of the shield clamp, the shield bottom has outwardly directed flange, and the shield clamp has an overlapping inwardly directed flange.

The seal apparatus also includes in certain embodiments an elastomeric spring element disposed between the shield top and the body, wherein the clamp is movable between a first position and a second position wherein the shield clamp is engaged with the base, wherein the spring element is compressed when the shield clamp is in the second position.

According to yet another aspect of the invention, a method for sealing a rotating processing container which rotates in a processing system is provided. The method includes providing a stationary seal member mounted on a processing system, the stationary seal having a plurality of circumferentially spaced annular sealing elements. The method also includes providing a rotating seal member mounted on the rotating processing container, the rotating seal member at least one annular sealing element. The sealing elements of the stationary seal member and the at least one sealing element of the rotating sealing member are contacted to form a rotating seal between the rotating processing container and the processing system.

According to another aspect of the invention, a method for sealing a rotating processing container is provided. The method includes providing a plurality of annular seals between the rotating processing container and a stationary portion of a processing system, wherein the plurality of annular seals define an annular space. The annular space is pressurized to provide an improved seal for the rotating processing container.

According to still another aspect of the invention, a method for heating or cooling a sample during transport of the sample into or out of a rotating processing container is provided. A seal apparatus including a rotating seal and a port for transport of a sample to the rotating processing container is provided, wherein the seal and the port define a space in contact with the port. The space between the seal and the port is filled with a material having a temperature which is at or below the temperature of the sample for cooling the sample, or a material having a temperature which is at or above the temperature of the sample for heating the sample. In preferred embodiments, the method provides for cooling of the sample by filling the space with waste materials generated by the processing methods, the waste materials being at or below room temperature. In certain embodiments the method provides cooling of the seal material during the transport of processing fluids into or out of the rotating processing container. The method includes providing a seal having an annular-shaped inlet/outlet port in fluid communication with the processing fluids, and filling the annular spaced with fluids that are cooler that the seal materials In yet another aspect of the invention, a spring is provided. The spring includes a hollow elastomeric cylinder having bowed side portions. The spring can be constructed of a certain height, width, thickness and side portion arc to provide a constant biasing force upon compression of the spring. The compression of the spring concurrently changes the height, width and arc. In certain embodiments, the spring includes an elastomeric material of relatively thin cross-section which has a geometry that delivers a relatively constant force over a wide range of deflection values. Preferably the spring has a cross-sectional shape that includes bowed side walls.

Thus the invention provides a seal apparatus including a plurality of annular seals, and/or a seal apparatus including at least one annular seal and a pressurized annular space concentrically spaced apart from the annular seal. Methods of using the seal apparatuses for sealing rotating containers also are provided.

These and other aspects of the invention will be described in further detail in connection with the detailed description of the invention.

DESCRIPTION OF THE PREFERRED EMBODIMENTS

Figure 1:
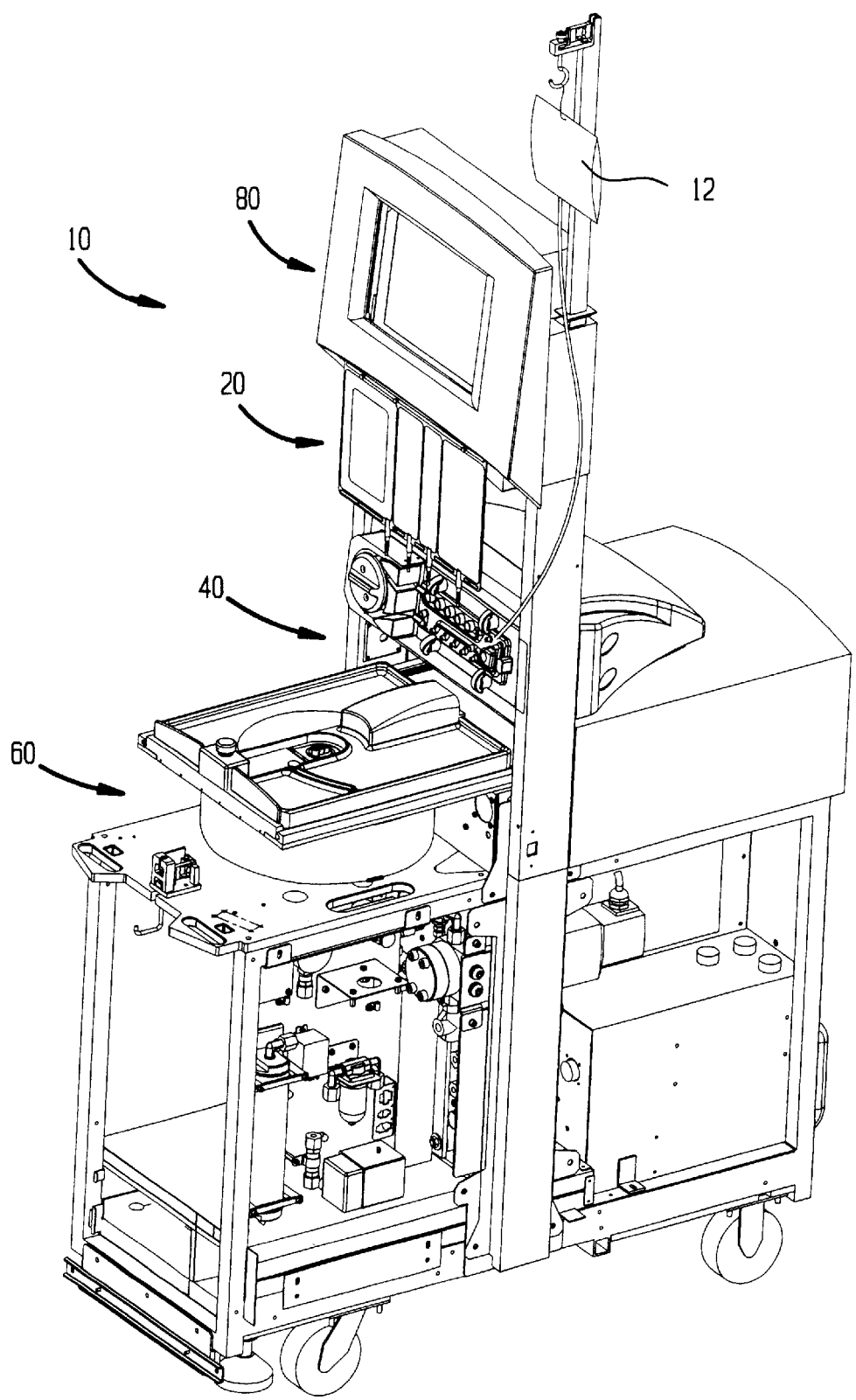
FIG. 1 is a perspective view of an interactive cell processing system.
Figure 3:
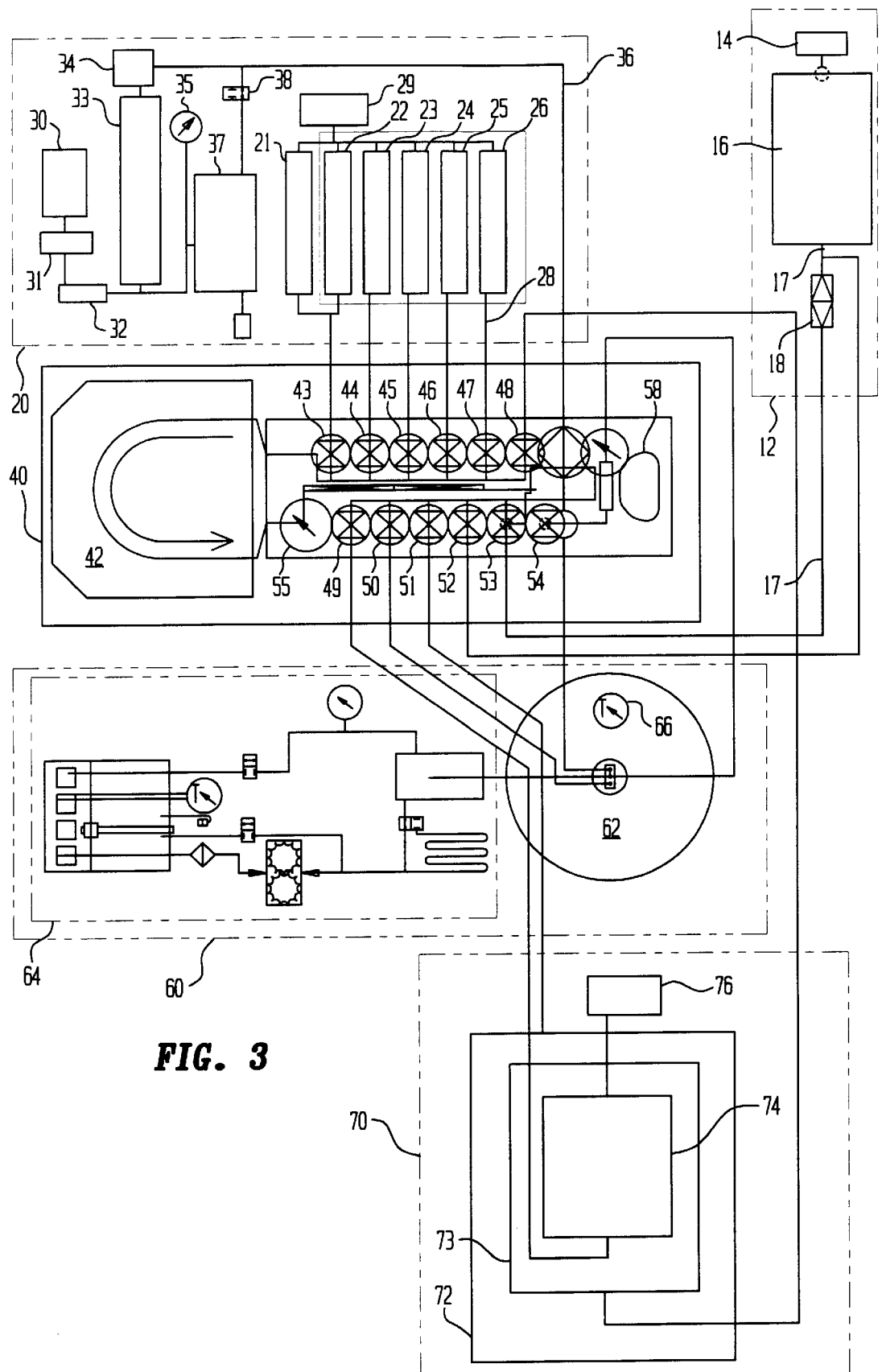
FIG. 3 is a block diagram of the interactive cell processing system of FIG. 1.

The preferred embodiments of the invention are described with reference to the drawings. Referring to FIGS. 1 and 3, an interactive cell processing system 10 includes a cell module 12, a supply module 20, a fluid distribution module 40, a processing module 60, a collection module 70 (not shown in FIG. 1) and a control module 80. These modules are operatively interconnected for processing biological cells in a sterile environment. Cell module 12 is constructed for a short term or long term storage of biological cells for processing. Supply module 20 includes several containers for storing different process chemicals including saline, or other fluids used for washing the processed cells and also includes sterile air. The containers are connected to fluid distribution module 40 by a set of conduits. Fluid distribution module 40 includes several valves and sensors for dispensing controlled amounts of the process chemicals from supply module 20 to processing module 60 and for dispensing a known amount of the biological cells from cell module 12 to processing module 60. Furthermore, fluid distribution module 40 is constructed to direct the process waste from processing module 60 to a waste container 72 and the processed cells to a cell storage container 74, both of which are located in collection module 70, while maintaining the purity and sterility of the cells. Control module 80 directs the entire process according to a selected algorithm.

Figure 2:
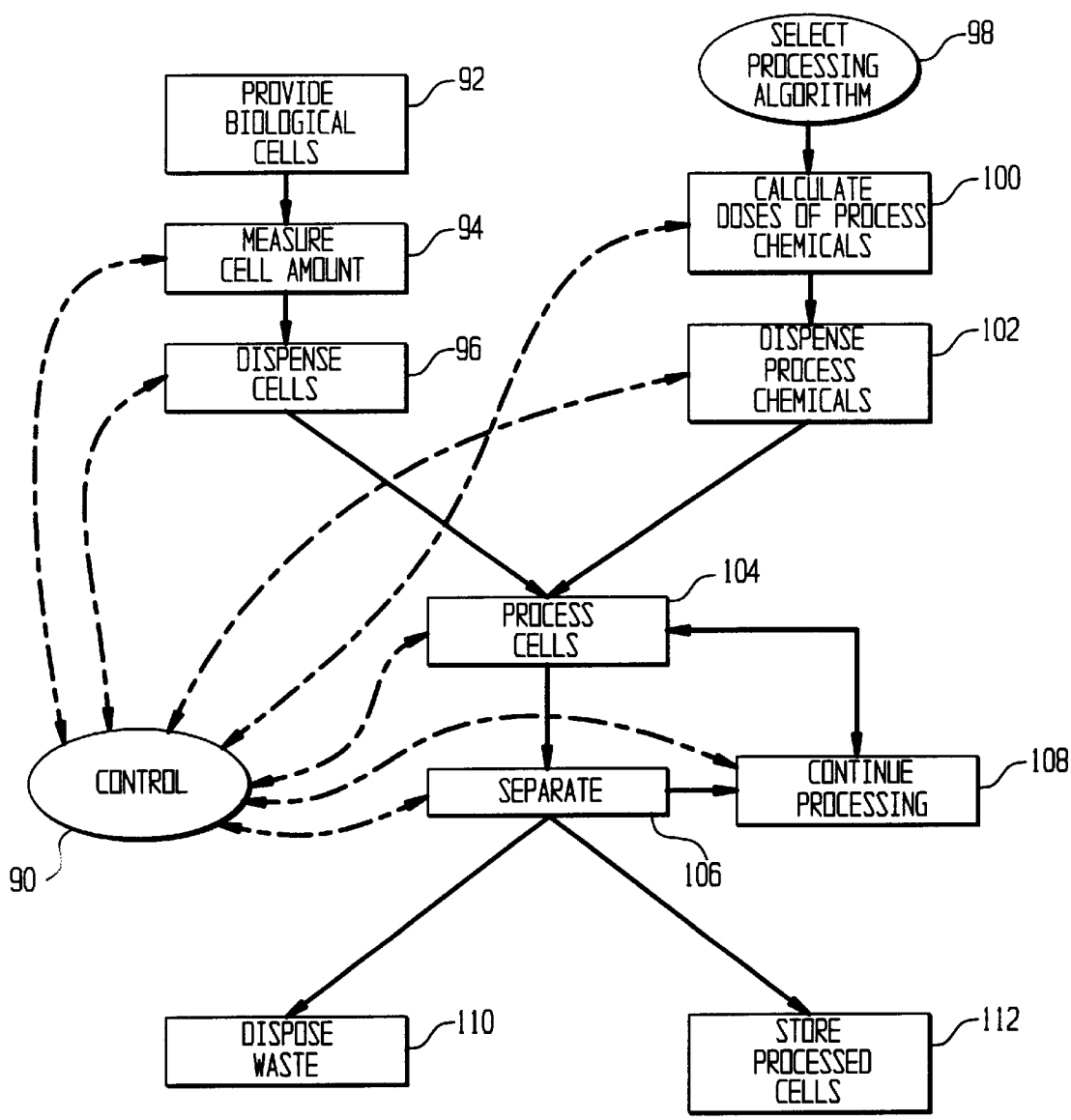
FIG. 2 is a conceptual flow diagram displaying operation of an interactive cell processing system.

In general, the operation of cell processing system 10 is shown in FIG. 2. Control module 80 executes a processing algorithm selected initially (98). Control module 80 includes a logic controller that receives real-time data from several in-line sensors arranged in a processing loop. A mass sensor (or a volume sensor) measures an initial amount of the provided biological cells (94) and sends the data to control module 80. Control module 80 controls the amount of cells dispensed to processing module 60 in accordance with the processing algorithm. Based on the provided amount of the biological cells, control module 80 also calculates the individual doses of the process chemicals (100) and directs a set of control valves to dispense the chemicals (102) in a selected order to processing module 60, again in accordance with the processing algorithm.

Control module 80 executes iteratively the processing algorithm. Control module 80 receives data from the individual sensors (e.g., a weight sensor, a volume sensor, a temperature sensor, an optical sensor, a resistance or capacitance sensor, a flow sensor, a pressure sensor or another sensor arranged to monitor the transferred matter in a liquid, gaseous or solid state). After dispensing the selected amount of one or several processing chemicals to processing module 60, control module 80 regulates the temperature and the time of processing and directs the processing module to agitate, mix or otherwise treat the cells with the process chemicals. Depending on the processing algorithm, control module 80 may manage one or several processing cycles. At the end of each cycle, processing module 60 may separate the processed cells from intermediate products and from the process waste. During the separation process, fluid distribution module 40 detects the fluid component being expressed from processing module 60 and directs the separated components to different containers for disposal (110) or for storage (112). Each processing cycle may use a different processing chemical and different processing conditions. Cell processing system 10 can also process different types of cells at the same time or sequentially. Furthermore, cell processing system 10 may also partially process biological cells and then store them in cell storage container 74 (shown in FIG. 3), which may include a temperature control system. The processed cells may be later automatically dispensed from cell storage container 74 and processed using another processing algorithm. The processed cells may also be grown in culture prior to another use.

Based on the starting weight of the biological cells, the controller calculates the dosage of the processing chemicals. Supply module 20 includes a weight sensor 29 for providing the weight of each process chemical to the controller. During the process, the controller confirms that correct amount of each process chemical has been transferred by measuring the change in the weight of the process chemical stored in supply module 20 and the initial weight of the chemical. The process chemicals in a fluid state are pumped through a 0.2 micron filter to assure sterility. A pressure transducer is mounted up-stream from the filter. If the fluids being pumped through the filter have a variable viscosity, the controller will adjust the pumping speed to yield a constant pressure drop across the filter membrane.

Processing module 60 is designed to assure identical processing conditions (e.g., pressure, temperature, mixing, processing time or other) for large and small amounts of the biological cells provided for processing. For this purpose, processing module 60 includes a processing chamber that has a variable volume design. Depending on the volume of the processed cells and other processing chemicals transferred into the processing chamber, the controller changes the chamber volume. The volume change is achieved by a movable wall that may be a membrane. Processing module 60 includes another pressure sensor for measuring the pressure inside the processing chamber and also includes a temperature sensor for measuring the temperature inside the processing chamber. Based on the data from the temperature sensor, a heat transfer system can provide or remove heat from the processing chamber.

Cell processing system 10 may process or separate cells and/or cell elements from different liquids or solids. Such cells and cell elements include, but are not limited to, erythrocytes (i.e., red blood cells); leukocytes (i.e., white blood cells, including lymphocytes, granulocytes, and monocytes); blood cell progenitors (e.g., primitive stem cells, burst forming units, reticulocytes, megakaryocytes, etc.); cell fragments (e.g., platelets, subcellular elements such as nuclei, debris, etc.); epithelial cells; endothelial cells; mesothelial cells; cells of normal tissues (e.g., liver cells, kidney cells, bladder cells, lung cells, pancreatic cells, embryonic cells, fetal cells, etc.); cells of abnormal tissues (e.g., malignant cells), and so forth.

Referring again to FIG. 3, in one preferred embodiment of the cell processing system, cell module 12 includes a weight sensor 14 arranged to weigh red blood cells provided in a bag 16. Tubing 17 connects bag 16 to a leuko filter 18 and to fluid distribution module 40. Supply module 20 includes a bag 21 with enzyme A1/B, a bag 22 with enzyme A2, a bag 23 with 140 Molar potassium phosphate dibasic (DPP), a bag 24 with polyethylene glycol (PEG), a bag 25 with storage solution, and a bag 26 with phosphate citrate isotonic (PCI). Each bag is connected by tubing 28 to fluid distribution module 40. Weight sensor 29 is constructed to weigh any of the above-mentioned fluids located in supply module 20. Supply module 20 also includes a compressor 30 connected via a filter 31 and a check valve 32 to air reservoir 33, which stores sterile air used for cell processing. Pressure switch and sensor 34 is in communication with air tubing 36, which delivers sterile air to an air filter located in fluid distribution module 40. A regulator 37, connected to a solenoid valve 36, regulates the air pressure provided to fluid distribution module 40 and to processing module 60. Fluid distribution module 40 includes a peristaltic pump 42, and twelve plunger valves 43, 44, . . . , and 54 connected to a set of conduits for distributing the process chemicals and the cells during the automated process. The logic controller can close or open any combination of the twelve valves to redirect the fluid flowing inside the conduits. A pressure sensor 55 measures the fluid pressure during the process, and a optical detector 58 monitors the fluid to and from processing module 60. Processing module 60 includes a centrifuge 62 and an expresser system 64. An infra-red (IR) temperature sensor 68 monitors the temperature of the process chemicals or the cells located inside centrifuge 62. Collection module 70 includes a waste bag 72, a saline solution bag 73, and a product bag 74. Collection module 70 also includes a weight sensor 76 connected to product bag 76 and arranged to weigh the processed red blood cells.

The controller controls the volume of the processing chamber of centrifuge 62 to assure identical processing conditions for large or small amounts of the red blood cells. The processing chamber includes a membrane for containing expresser fluid. For small volumes, expresser system 64 pumps expresser fluid into the chamber until the pressure transducer at the chamber signals a full condition. This pre-filling step assures that different amounts of red blood cells are subjected to the same accumulated centrifugal force and mechanical stresses due to packing. Otherwise, smaller amounts would spin longer and pack harder as the expresser fluid fills the processing chamber during the expression step.

During the process, the controller receives input from IR temperature sensor 66, which measures the temperature of the RBCs. If the temperature is less than the set point, expresser of system 64 increases the temperature of the expresser fluid. Conversely, if the temperature is greater than the set point, expresser of system 64 decreases the temperature of the expresser fluid. A control loop continuously monitors the temperature of the processed cells.

Processing module 60 also includes a second pressure transducer that monitors the pressure of the sterile air on the rotating seal. If the seal is working, this pressure only fluctuates slightly between established limits. If the pressure drops below the established threshold, a warning condition is initiated that calls for a check of the rotating seal as well as other possible causes of failure.

Expresser fluid system 64 included a third pressure transducer that measures the pressure of the expresser fluid which is an indirect measure of the pressure on the red blood cells. The controller adjusts the expresser pump speed to assure that pressure is within accepted limits and cells are protected from damage. If the pressure is too low, the pump rate is increased to speed up the expression cycle. If the pressure is too high, the pump is slowed down to protect the cells from excessive pressure. This also protects the seal from excessive pressure as well.

Optical sensor 58 sensor monitors the color and the turbidity of the transferred fluids. Specifically, optical sensor 58 also monitors the supernatant expressed from the centrifuge chamber. When red cells are detected in the supernatant, the controller responds by stopping the expresser pump to avoid losing any cells to waste or responds by switching valves to collect the cells in a separate storage bag depending on which cycle is being performed.

The cell processing system can be used, for example, in methods of enzymatically converting blood type or inactivating pathogens. Certain methods of enzymatically converting blood type are set forth in U.S. Pat. No. 4,330,619, 4,427,777 and 4,609,627 by Goldstein.

Processing module 60 includes a "rotating seal" that is a seal created between moving and stationary components of the centrifugal element. The seal acts as a barrier between the interior portion of the system in which processing occurs, which is desirably maintained as microbe-free as possible, and a nonsterile environment which, at least during a portion of the operation of the system, is in communication with the environment external to the system. The rotating seal also prevents the dispersal of microbes (e.g. viruses) which may exist in a cell sample into the external environment.

The rotating seal comprises an upper element and a lower element, wherein one element rotates during at least a portion of the operation of the cell processing system. The rotating seal surrounds an axial opening through which cells and/or cell elements and processing materials are intended to pass during processing.

Figure 4:
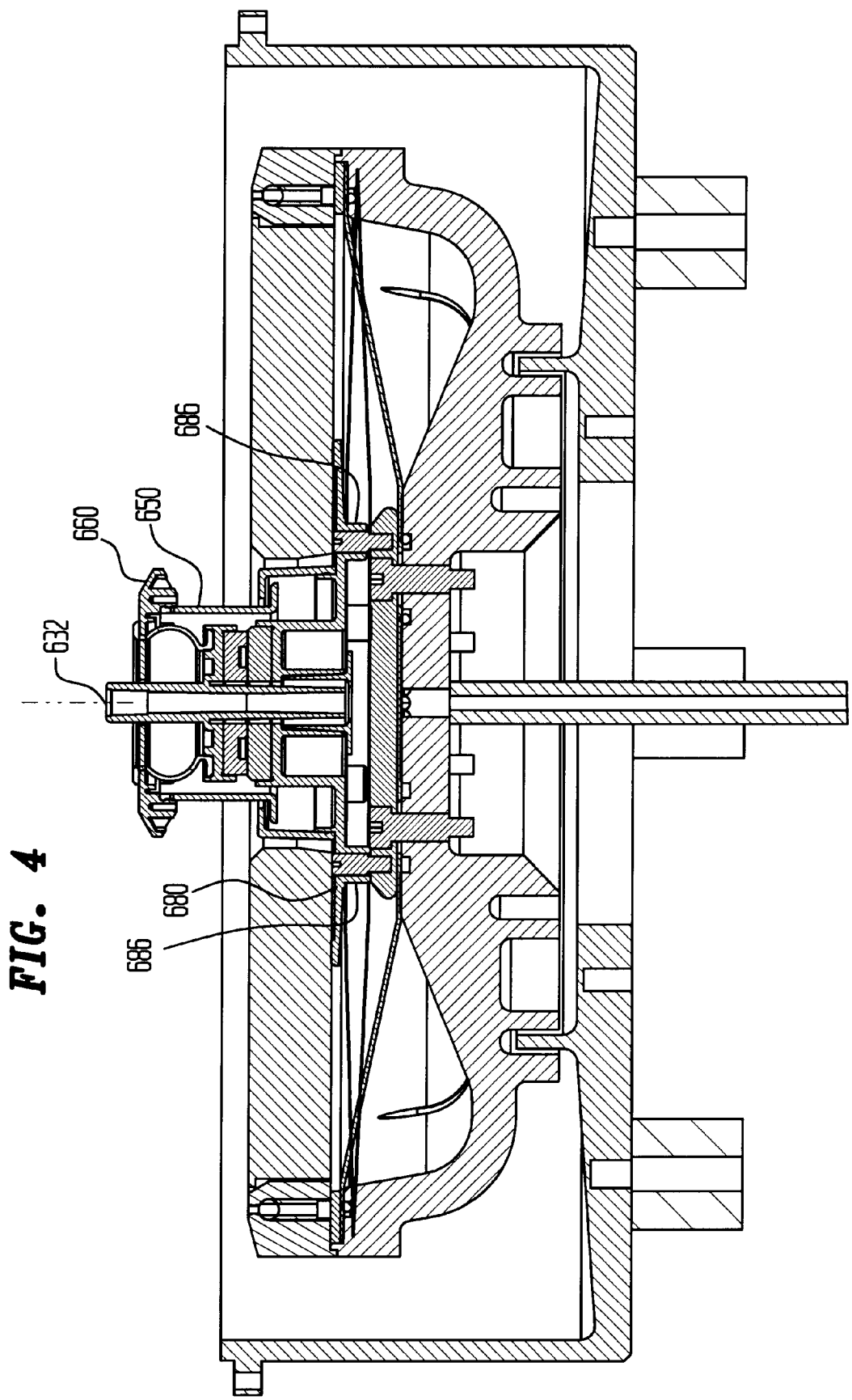
FIG. 4 is a cross-section view of a centrifuge bucket and chuck which depicts the mounting of the rotating seal assembly in the centrifuge.

FIG. 4 is a cross-section view of a centrifuge bucket and chuck which depicts the rotating seal apparatus seated in the chuck. Protruding from the top of the centrifuge bucket are the first port 632, the header shield top 660 and the header shield bottom 650. The rotating seal apparatus is mounted to the chuck by mounts 686 protruding from the base 680. The mounts mate with opposing projections fixed to the chuck, thereby transmitting the rotating force of the chuck to the lower parts of the rotating seal apparatus and the processing container to which the base 680 is mounted.

Figure 5:
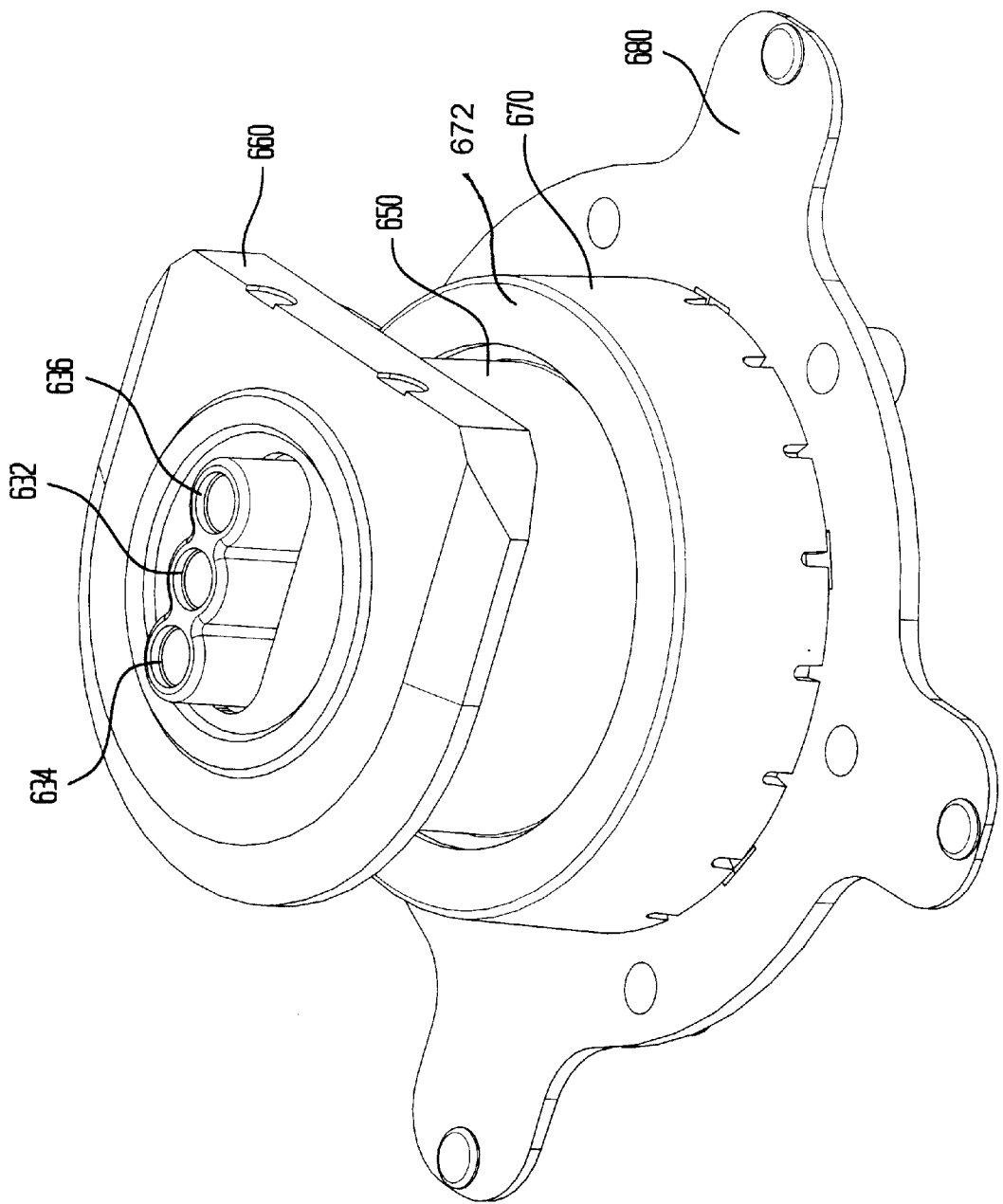
FIG. 5 is a perspective view of the exterior of the rotating seal apparatus.
Figure 6:
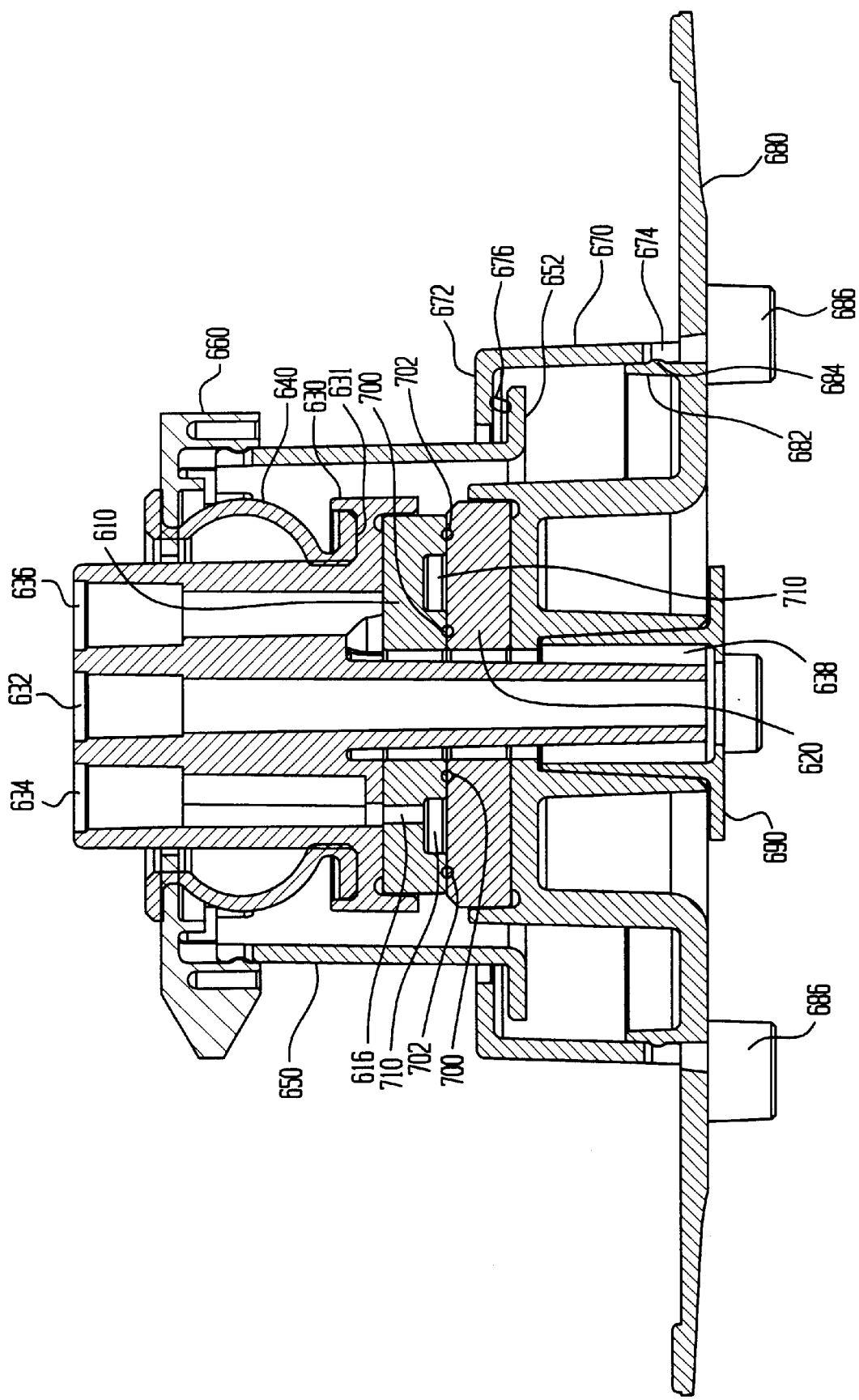
FIG. 6 is a cross-section view of the rotating seal apparatus.

FIG. 5 depicts an assembled rotating seal apparatus. The header shield assembly is comprised of the shield top 660, the shield bottom 650 and the shield clamp 670. The shield clamp includes an inwardly directed flange 672 which overlaps an oppositely directed flange on the shield bottom. In alternative embodiments, the shield clamp can have a smaller diameter than the shield bottom, and have an outwardly directed flange to overlap an inwardly directed flange of the shield bottom. The shield clamp is mounted on the base 680, which in turn is mounted on a processing container. As depicted in FIG. 6, the base 680 includes a flange 682 which includes a outwardly directed protrusion 684. When the shield clamp is mounted on the base, the protrusion 684 fits into the indentation 674 on the inside surface of the shield clamp, thereby holding the header shield assembly together and preloading the spring 640 to create contact between the sealing surfaces. Ports 632, 634 and 636 are included as inlets and outlets for materials passing through the rotating seal apparatus to a processing container and for providing materials to internal portions of the rotating seal apparatus. These are described in greater detail below.

Referring to FIGS. 6–9, the rotating seal comprises an upper sealing member 610 and a lower sealing member 620.

Figure 7:
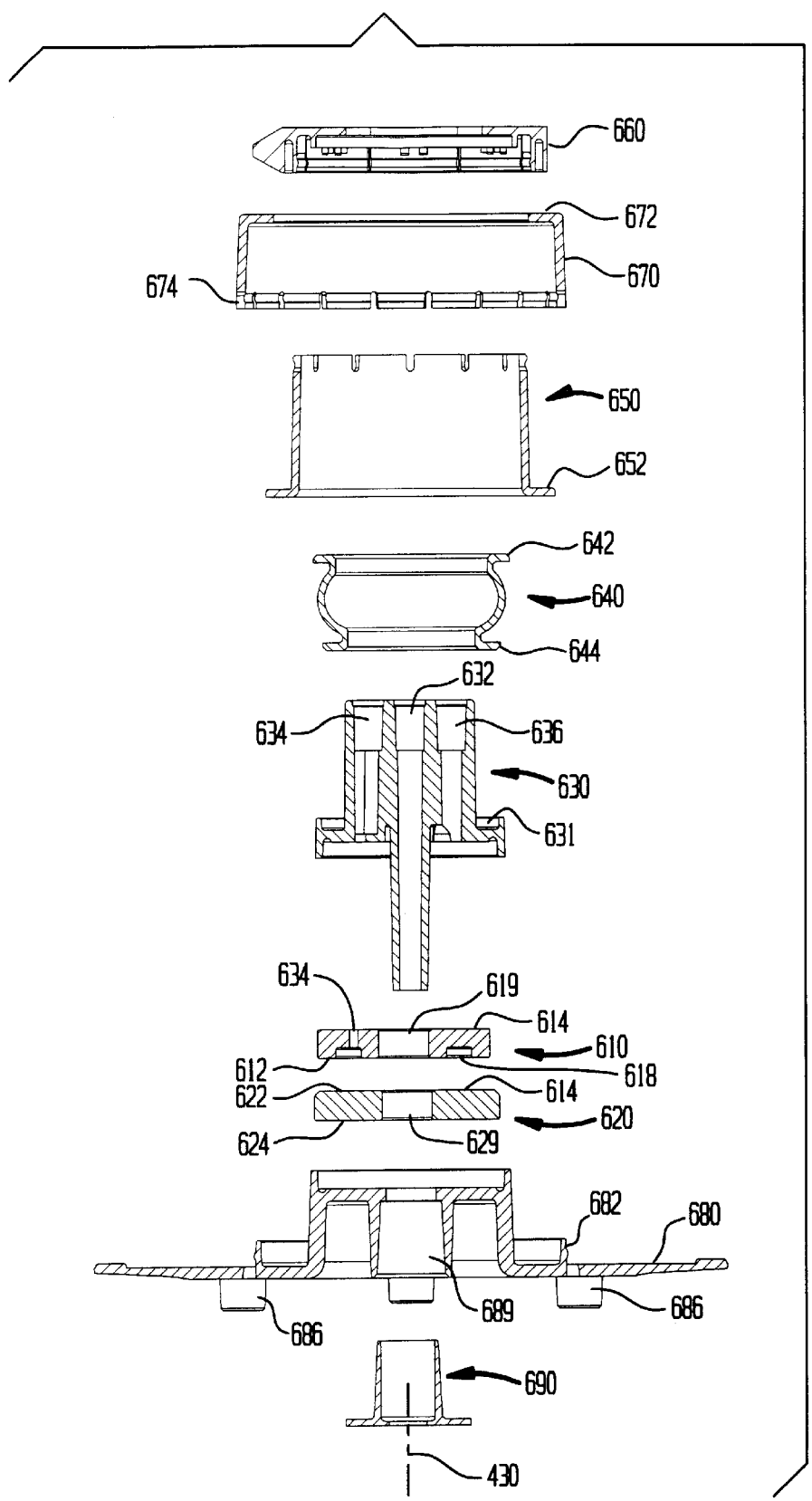
FIG. 7 is an exploded cross-section view of the rotating seal apparatus.
Figure 8:
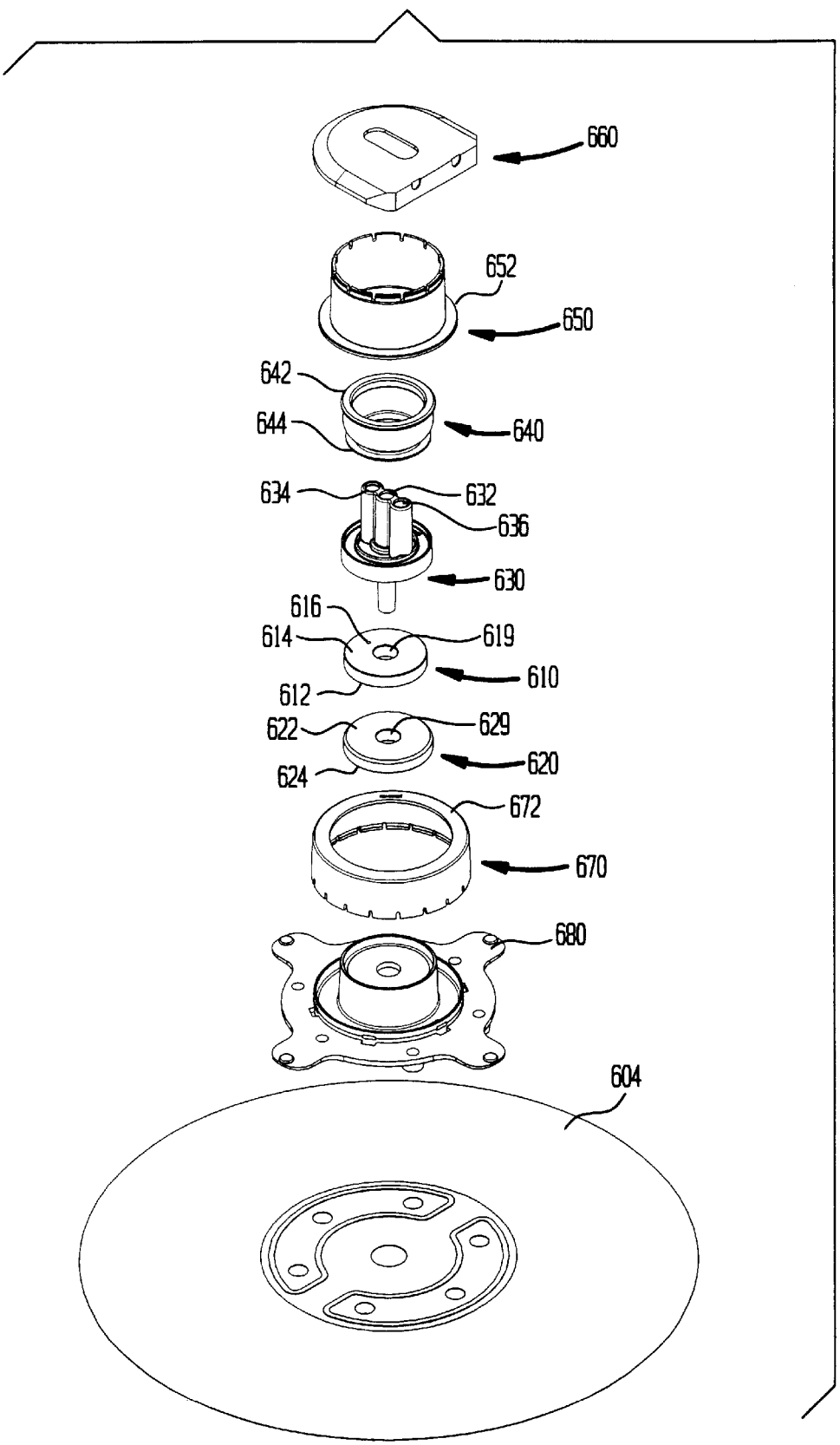
FIG. 8 is an exploded top perspective view of the rotating seal apparatus and processing container.
Figure 9:
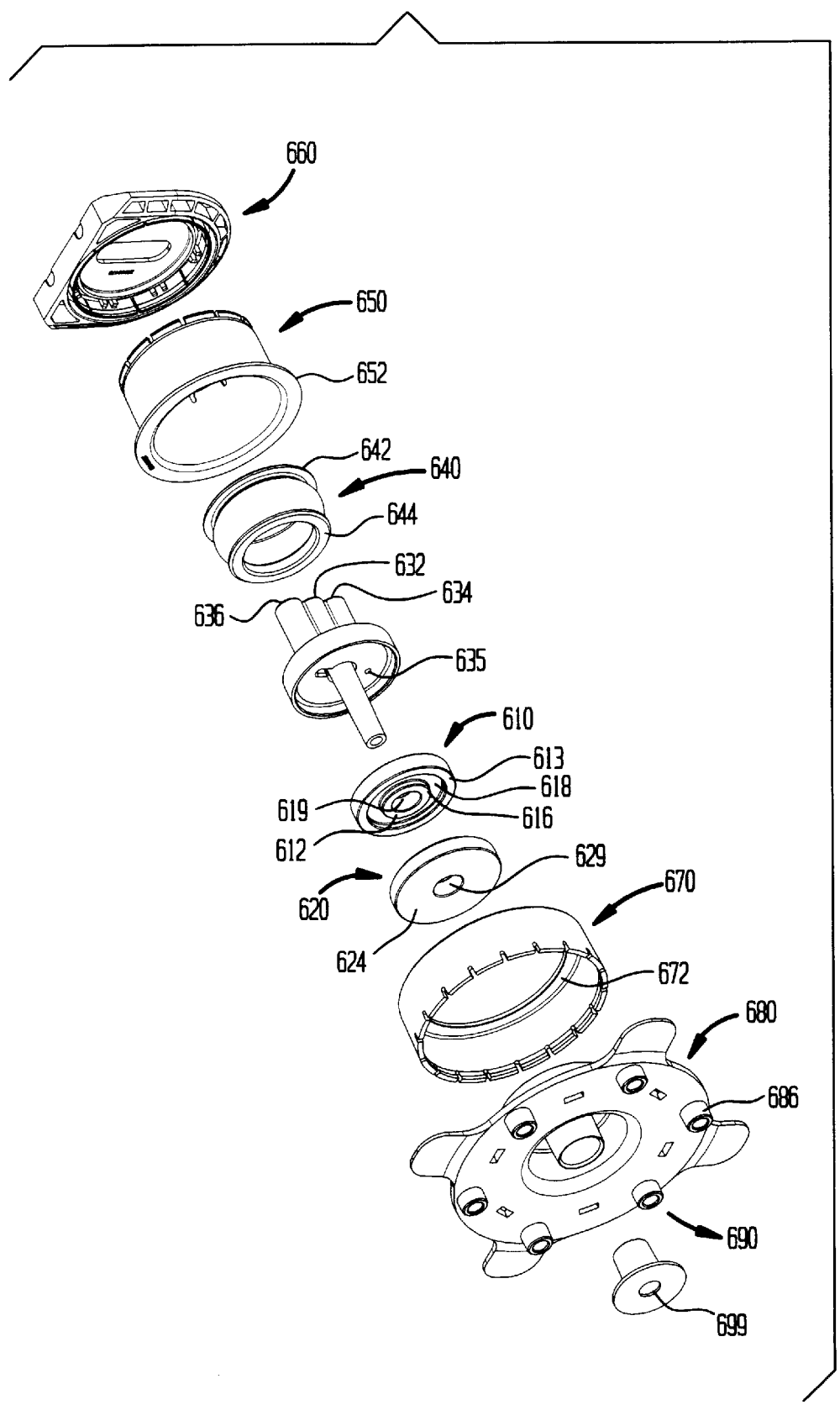
FIG. 9 is an exploded bottom perspective view of the rotating seal apparatus.

As shown in FIG. 6, when biased together, the contact of the sealing members creates a plurality of annular seals. A first seal 700 is formed between sealing surfaces 612 and 622, and a second seal 702 is formed between sealing surfaces 613 and 622. As shown in FIGS. 6, 7, and 9, the sealing face of the upper sealing member 610 is formed into two sealing surfaces 612 and 613 as lands surrounding a groove 618. The groove forms the upper boundaries of an annular space 710 between the concentric seals 700, 702. The groove can be cut from or molded into the upper sealing member as desired.

In the embodiment depicted in FIGS. 6–9, the sealing face of the lower sealing member 620 is not formed into lands and grooves; rather, the sealing surface 622 forms the plurality of concentric seals in combination with the sealing surfaces 612 and 613, and forms the annular space in combination with the groove 618. In alternative configurations of the rotating seal, the lower sealing member can include the topography of lands and grooves and the upper sealing member can be planar. In still other embodiments, both the upper and the lower sealing members can include lands and grooves. The sealing surfaces preferably are planar, although other geometries also can be used provided that a close fit can be achieved between stationary and rotating members of the rotating seal.

The upper and lower sealing members 610, 620 also each define axial openings 619 and 629, respectively. Upon assembly of the sealing members in axial alignment, the axial openings, the first seal, the annular space, and the second seal are positioned concentrically relative to each other.

The annular space 710 can be in communication with the external environment, and preferably is in gaseous communication through the channel 616. The channel can be formed in either of both of the sealing members 610, 620. In preferred embodiments the annular space 710 constitutes a sterile chamber. Further seals, separated by additional annular spaces, may also be included in the rotating seal apparatus.

The rotating seal apparatus depicted in FIGS. 5–9 also includes a body 630 having ports 632, 634 and 636 which serve as inlets and/or outlets for material passing into and out of a processing container to which the rotating seal apparatus is mounted. The first port 632 traverses the axial opening of the rotating seal apparatus, terminating at plug 690. The first port preferably serves as an inlet into the processing container for cells which are to be processed. The first port additionally serves as the outlet for processed cell following the execution of processing steps. The first port can be connected to a number of tubes, fluid handling manifolds, valves etc. as will be known to one of ordinary skill in the art.

The fluid port 636 is in fluid communication with the annular space 638 bounded by the exterior surface of the first port and the walls of the axial openings 619, 629, 689, 699 of the upper sealing member 610, lower sealing member 620, base 680 and plug 690. The fluid port 636 connects to the annular space below. In certain embodiments, the fluid port 636 and annular space 638 are used for passage of processing materials such as wash solutions, buffers, enzymes and the like into the processing container. The fluid port 636 and annular space 638 also are used for passage of waste materials out of the processing container. This outlet function also serves a temperature regulation function. As the sealing members of the rotating seal apparatus turn against each other, local frictional heating of the rotating seal apparatus above room temperature occurs. Passage of waste materials, which are at temperatures at or below room temperature, out of the processing container through the annular space 638 and fluid port 636 contact the first port 632 and thereby lower the temperature of the first port. The cooled first port does not heat cells as an uncooled port would upon passage of processed cells out of the processing container through the first port. As with the first port, the fluid port can be connected to a number of tubes, fluid handling manifolds, valves etc. as will be known to one of ordinary skill in the art.

The gas port 634 is in gaseous communication with the annular space 710 between the concentrically spaced seals 700, 702. The gas port preferably serves as the inlet for providing sterile air (or other gas) to pressurize the annular space 710. The gas port can be connected to a number of tubes, filters, valves etc. for providing a sterile supply of gas as will be known to one of ordinary skill in the art.

The base 680 and plug 690 fit together as depicted in FIG. 6. A single unitary base/plug combination also could be used as desired. The base 680 serves both as a mount for the lower seal member 620 and as a mount for the shield clamp 670 by means of the flange 682 and protrusion 684. The base is mounted on the processing container to provide fluid communication of the first port 632 and the fluid port 636 with the interior of the processing container. A plurality of mounts 686 can pass through sealed portions of the processing container can be mounted on the chuck of a centrifuge to communicate rotation of the centrifuge chuck to the base, processing container and lower seal member of the rotating seal apparatus. Other means of securing the rotating seal apparatus and processing container to the centrifuge for providing rotation to the processing container are well known to one of ordinary skill in the art.

The spring 640 is depicted in FIGS. 6–9, and comprises a hollow generally cylindrical-shaped elastic member having bowed sides. The spring is disposed between the header shield top 660 and the body 630. As depicted, the spring is provided with flanges 642, 644 at its upper and lower ends. The lower flange 644 fits into an annular recess 631 formed in the body. The top flange 642 fits against the header shield top. Upon assembly of the rotating seal apparatus by snapping the header shield clamp against the base, the spring is deflected from a first position to a second position which provides a "pre-load" of contact forces to the seal members. When the rotating seal apparatus is enclosed in a centrifuge, the spring can be deflected to a third position of greater deflection which provides an increased contact force to the seal members, thereby creating an enhanced seal.

In contrast to helical springs, the cylindrical spring of the invention provides a constant biasing force over a wide range of compression. The spring has a height h which describes the axis of deflection or compression, a width w which describes the diameter of the spring in nondeflected or deflected positions, an thickness t and an arc a. The height, when the spring compressed from the first position, is reduced from $h_1$ to $h_2$. Similarly, the spring width is increased on compression from $w_1$ to $w_2$. The spring provides constant biasing force over a Δh of at least 10%, preferably at least 20%, more preferably at least 30% and most preferably at least 50%. Further, the spring provides constant biasing force over a Δw of at least 1%, preferably at least 2%, more preferably at least 5% and most preferably at least 10%. The range of compression over which the biasing force is constant also can be described by the ratio of Δh:Δw, wherein the spring experiences a relatively large Δw for a corresponding Δh. The thickness t of the spring should not be too great as to hinder the bowing of the cylinder sides on compression of the spring. A range of thicknesses and arcs will be useful to provide proper bowing; these ranges can easily be determined by one of ordinary skill in the art with no more than routine experimentation, and may depend on the particular elastomeric material chosen for manufacture of the spring. The appropriate thickness and arcs can be expressed in terms of ratios of h:t and h:a, when h, t, and a are measured in deflected or nondeflected positions.

The rotating seal apparatus of the invention may be validated as "closed" devices, and thereby produce product with longer shelf life than prior art rotating seal devices. A second annular seal provided circumferentially around the first or inner seal provides further assurance of seal integrity. To still further promote the sterility of the interior of the seal and processing container, the annular space 710 can be filled with sterile air and, further, a pressure differential may be created such that the sterile air in the annular space is at a pressure higher than the pressure in the surrounding chamber formed by the header shield. Therefore, the flow pattern of the hydrodynamic film may be directed away from the sterile interior and toward the spaces exterior to the rotating seals. Further, the chamber formed by the header shield may be provided with a steady supply of sterile air at a pressure lower than that in the annular space 710 but higher than ambient pressure. This "double redundancy" of the two surrounding sterile chambers at graduating pressures is theoretically analogous to that used in the design of clean rooms for sterile filing of pharmaceuticals.

The annular space 710 can be filled with a gas or liquid; preferably, the gas or liquid is substantially sterile. The enclosed space thereby creates a barrier to microbes or other particulate materials passing into or out of the interior of the cell processing system. The gas or liquid may be introduced into the enclosed space via a channel which passes through or between the upper and lower elements. For example, referring to FIG. 6, air can be pumped through a 0.2 micron filter to assure sterility, and then be pumped through the gas port 634 to the channel 616 and into the annular space 710. Optionally the annular space 638 formed between the inner seal 700 and the first port 632 can be pressurized, for example when the annular space 638 is not conveying reagents into the processing container 604 or waste liquids out of the processing container. Preferably the annular space 710 is pressurized with sterile air at pressure slightly above atmospheric pressure. For example, it has been determined that an air pressure of approximately 0.25 PSIG suffices to provide a pressurized environment in the annular space to enhance the sealing function of the sealing members. Other pressures and gases can also be employed in similar fashion as will be evident to one of ordinary skill in the art. In alternative embodiments, the annular space is pressurized relative to the exterior and interior of the rotating seal apparatus by evacuating the exterior and/or interior (e.g. the space inside the header shield and/or the annular space 638, respectively) by means of a vacuum pump or other device which creates a pressure differential.

In certain embodiments of the invention, the sterile air may be provided from a pressurized tank that uses a precise pressure regulating valve to reduce the tank pressure to a level that is slightly positive relative to ambient pressures (e.g. 0.25 PSIG). A computer software controlled "watchdog circuit" may be placed in communication with the annular space 710 to indicate, in a detectable manner, if and when undesirable pressure levels in the interior of the cell processing system occur. Furthermore, alterations in pressure in the annular space, detectable by a pressure monitor, may alert a system operator that one of the sealing elements has been breached and/or the barrier function of the annular space has been disrupted.

A second redundant sterile chamber can be created by the header shield assembly (shield top, shield bottom and shield clamp) that surrounds both the first and the second seal members. Sterile air may be supplied to this chamber at a pressure that is less than that of the annular space between the seals but greater than the surrounding ambient condition. The flow of air is from areas of higher pressure to areas of lower pressure. Therefore, the flow of sterile air may be directed from the inside of the seal and in an outward direction. Potential microbial contamination may thus be swept away from the sterile interior of the seal by this flow vector.

A serpentine seal 676 is formed between the close tolerance of the opposing flanges 672, 652 of the shield bottom and shield clamp. The serpentine seal may create shear forces between the surfaces of the flanges which prevent particulate material from the outside the shield from entering the shield and thus the seal assembly. In general, the serpentine seal acts as a physical barrier, if not a seal, to contaminants external to the rotating seal apparatus.

In additional embodiments, the rotating seal apparatus can be formed of two concentric lip seals or two concentric barrel seals. Between lip seals or barrel seals is an annular space analogous to annular space 710. The annular space is in communication with a source of gas or liquid (e.g, sterile pressurized air). Additional seal types will be known to one of ordinary skill in the art.

In operation, the rotating seal apparatus is provided as a preassembled device, properly preloaded by spring biasing force to create seals between the upper and lower sealing members. The rotating seal apparatus is placed in a cell processing system centrifugal device, for example by mounting it on a centrifuge chuck by the mounts 686. Closing the centrifugal device causes the compression of the spring to a third position which forces the seals into closer contact than the preload contact and maintains the close contact during rotation. The ports 632, 634 and 636 are joined to an appropriate set of tubes, optionally via connectors, to provide cells, processing materials, sterile air, etc. to the rotating seal apparatus and processing container. Upon rotation of the centrifugal device, the upper seal member, body, header shield top and bottom remain stationary and the lower seal member, base (and attached processing container), and header shield clamp rotate while the integrity of the seals are maintained.

The sealing surfaces of the upper and lower sealing members can be formed or fabricated of a variety of materials well known to one of ordinary skill in the art. Suitable materials include ceramics, carbon phenolic, graphite and graphite derivatives, lubricious plastic materials such as nylon, delrin, teflon, rulon, bronze and alloys thereof, stainless steel, carbon nitrites, etc. The sealing members can be manufactured as a single piece or as a separate sealing portions and support portions of the sealing member. The sealing members can be manufactured, for example, by injection molding or other method of fabrication, followed by making the sealing surfaces flat (e.g. by grinding or lapping) and polishing. The sealing members thus treated have sealing surfaces which when contacted essentially prevent fluid passage. Preferred materials include ceramics and carbon phenolic compounds. In a preferred embodiment, the upper and lower sealing elements are formed of ceramic which is lapped and polished.

Other parts of the apparatus are constructed of various polymeric materials which preferably are FDA-approved for medical devices. The header shield top 660, the header shield bottom 650 and the header shield clamp 670 are preferably constructed of high impact polystyrene (HIPS), although any rigid plastic known to one of ordinary skill in the art which has some elastomeric properties can be used. The body 630 and the base 680 are preferably constructed of polycarbonate which provides good strength and stability. Other like materials can also be used.

The spring 640 is constructed of an elastomeric material, and preferably is constructed of a medium durometer silicon material such as thermoset silicon or liquid injection molding silicon. One also could use various rubber materials for the spring, preferably materials which are FDA approved for medical devices.

The present invention may be used in a variety of cell and cell element processing procedures, including collection and/or washing or red blood cells, platelets, lymphocytes, granulocytes, monocytes, and stem cells (e.g., from peripheral blood, bone marrow, or cord blood), as well as other methods such as viral inactivation. In preferred embodiments, the cell processing system may be used in methods of enzymatically converting blood type. Methods of converting blood type are, for example, set forth in U.S. Pat. Nos. 4,330,619 and 4,609,627 by Goldstein. Other uses for the rotating seal portion of the apparatus will be known to one of ordinary skill in the art.

EQUIVALENTS

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

What is claimed is:

1. A seal apparatus comprising:
   a body comprising a first portion and a second portion, wherein an axially aligned first opening acting as a first port is positioned through the first portion and the second portion, and wherein the first portion includes a recess and a second opening acting as a second port positioned adjacent and parallel to the first port opening;
   a first annular rotating seal member positioned within the recess, the first annular rotating seal member having a non-sealing face, and a sealing face which defines a plurality of concentrically spaced annular sealing surfaces having an annular space therebetween, the member further defining an axial opening, and
   a second annular rotating seal member having a non-sealing face, and a sealing face which defines at least one annular sealing surface, the member further defining an axial opening, wherein
   the first annular rotating seal member and the second annular rotating seal member are axially aligned, the annular sealing surfaces of the first annular rotating seal member and the second annular rotating seal member are placed in contact to form a plurality of spaced apart seals, and
   at least one of the non-sealing faces of the first annular rotating seal member and the second annular rotating seal member define a channel in gaseous communication with said annular space and with the second opening of the first portion of the body.

2. The seal apparatus of claim 1, wherein the annular sealing surfaces are substantially planar.

3. The seal apparatus of claim 1, wherein the annular sealing surfaces of the first annular rotating seal member and the second annular rotating seal member are biased together by a bias element.

4. The seal apparatus of claim 3, wherein the bias element is an elastomeric spring element.

5. The seal apparatus of claim 1, wherein the annular sealing surfaces of the first annular rotating seal member and the second annular rotating seal member are formed of a material selected from the group consisting of ceramics and carbon phenolic.

6. The seal apparatus of claim 5, wherein the annular sealing surfaces of the first annular rotating seal member and the second annular rotating seal member are formed of ceramic.

7. The seal apparatus of claim 1, further comprising a base having an axial opening and a processing container having a top defining an axial opening, the base mounted in axial alignment on the top of the processing container, the second annular rotating seal member mounted in axial alignment on the top surface of the base, wherein the first port is in fluid communication with the interior of the processing chamber.

8. The seal apparatus of claim 7, wherein the first port extends through the axial openings of the first and second annular rotating seal members and the base.

9. The seal apparatus of claim 8, wherein the body further comprises a fluid port in fluid communication with a space defined by the first port, the first and second annular rotating seal members and the axial openings of the base.

10. The seal apparatus of claim 7, further comprising an outer shield defining a space between the outer shield and the body, the base and the first and second annular rotating seal members.

11. The seal apparatus of claim 10, wherein the outer shield comprises a shield top, a shield bottom and a shield clamp, wherein the shield top is releasably mounted on the shield bottom, and wherein the shield bottom and the shield clamp have overlapping flanges which form a serpentine seal.

12. The seal apparatus of claim 11, further comprising an elastomeric spring element disposed between the shield top and the body, wherein the clamp is movable between a first position and a second position wherein the shield clamp is engaged with the base, wherein the spring element is compressed when the shield clamp is in the second position.

\* \* \* \* \*